Aug. 4, 1936. C. E. HUBER Plant Pat. 189

BARBERRY PLANT

Filed Dec 5, 1934

DISCOVERER
CARLTON E. HUBER
BY
J. W. Schmied
ATTORNEY

Patented Aug. 4, 1936

Plant Pat. 189

UNITED STATES PATENT OFFICE

189

BARBERRY PLANT

Carlton E. Huber, Groesbeck, Ohio

Application December 5, 1934, Serial No. 756,016

1 Claim. (Cl. 47—59)

My invention or discovery relates to barberry bushes and particularly to a new strain or variety of barberry bush which I have discovered, reproduced and propagated. The new barberry has definite and peculiar characteristics which led to the original discovery of the single parent plant by me about twelve years ago. It was first noted growing in a block of seedlings of *Berberis thunbergii*. Its peculiarities attracted my attention and caused me to reproduce it by asexual methods. It has been propagated and tested in the nursery row for a number of years and its characteristics have been found to be fixed and asexually reproducible. It can be propagated true to type by grafting or by cuttings, but not from seeds.

Figure 1:
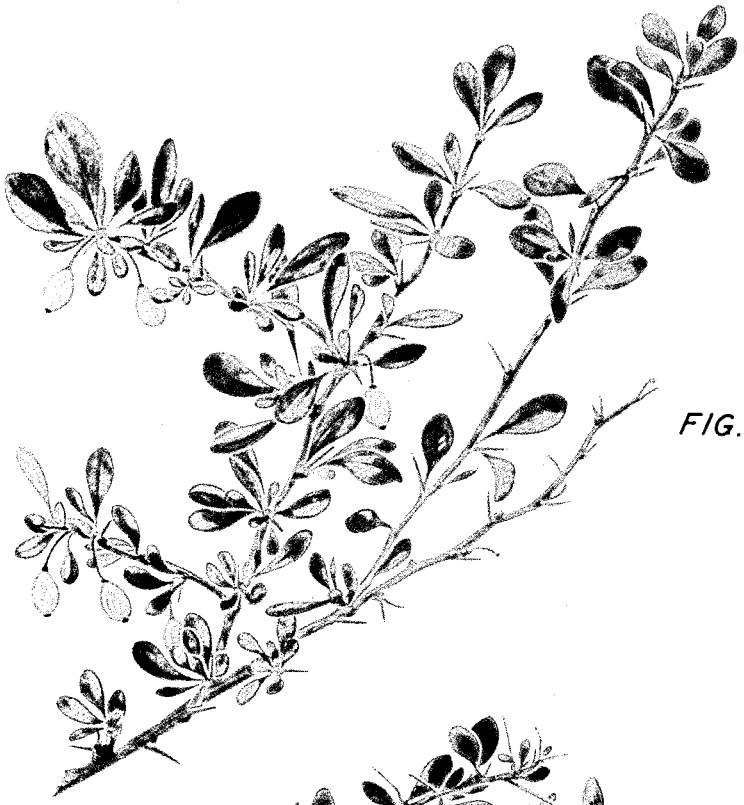
Figure 2:
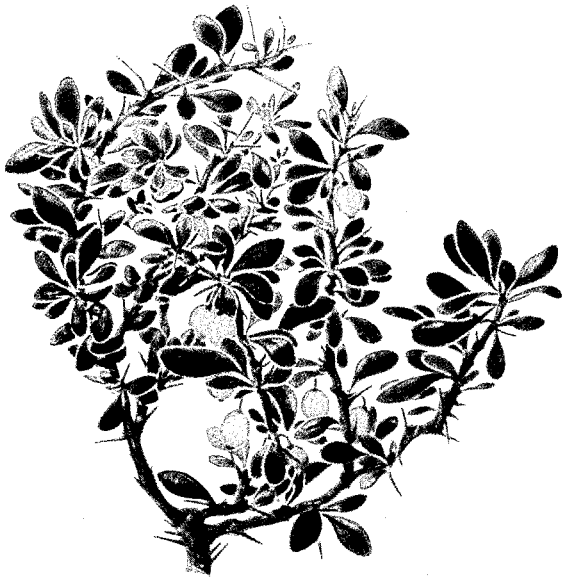

In the attached drawing, Fig. 1, given for comparison purposes, is as nearly as possible a reproduction of a twig of the parent barberry as cut about October 1 and Fig. 2 is a reproduction of a twig of the new barberry cut about the same date. However, it has not been possible to bring out all of the differences in appearance although these are readily apparent to the eye when viewing the actual plant.

The foliage of the new barberry as compared to *Berberis thunbergii* is more abundant, darker and more uniform green in late autumn and of a peculiar curled appearance. The leaves are smaller, averaging in area no more than about one-fourth the area of the leaves of the parent. The leaves are also thicker and have a peculiar dark green shiny appearance until late fall. In a general way the color and texture of the foliage in early autumn somewhat resembles that of a healthy azalea plant, although, of course, the individual leaves are much smaller and of somewhat different shape.

The plant puts forth its leaves very early in the spring and the leaves assume a beautiful red and yellow color in the very late autumn.

The most striking characteristic of the new plant is its habit of growth. Its plant growth is slower than the parent, the branches are heavier and less straight, and young shoots are produced with great freedom. Without shearing or pruning it produces very compact, uniform plants of approximate globe shape but usually slightly flattened on the top. This globe shape is assumed by the plants when young, it is manifest in the first year and is a quite distinctive feature during the second year and at all times thereafter. The long curving or straight shoots of six inches to several feet in length commonly developed by the usual forms of barberry are entirely absent. This is a distinctive feature of the plant. Two year grafted plants average around 6 to 9 inches in height in good soil and are as broad as their height. They have many terminal buds. In Fig. 2 of the drawing the natural appearance of the portion of the bush shown is reproduced as nearly as possible and represents about 2 years growth made without pruning or shearing at any time. In ordinarily good soil a year's growth is usually no more than 1 to 4 inches whereas under similar conditions the annual growth of the parent plant greatly exceeds this. The notably compact and distinctive appearance of the new plant as an entirety cannot be effectively illustrated but may be fully appreciated by imagining from 12 to 20 branches each of the approximate dimension shown in Fig. 2 all located in and occupying a spherical space no greater than a 9 or 10 inch globe. Although a slow grower with respect to the increase in length of any individual twig the plant is not much slower than common barberry when the total growth of all the twigs is considered because the terminal buds and branches at which growth occurs are much more numerous.

The fruits or berries on mature plants are more abundant, slightly larger and a shade darker than *Berberis thunbergii* under similar growing conditions. In shape they differ little but are slightly more nearly round, i. e. their thickness is a trifle greater in comparison with their width. No attempt has been made to show the relative size or color of the fruits in the drawing.

A feature of the new plant is its extreme hardiness. Many specimens have withstood severe drought and temperatures from −24° F. to 110° F. in the open field without artificial protection and with no apparent damage. As an ornamental or hedge plant it has many desirable features.

What is claimed is:

The barberry plant as shown and described, characterized by slow compact globular form of growth even in young plants of one and two years age, free branching habit, absence of shoots of annual growth over a few inches in length, presence of several branches every few inches, abundant foliage extending into the interior of the plant, and leaves remaining a uniform green until late in the autumn.

CARLTON E. HUBER.